US008911603B2

(12) United States Patent
Winkler et al.

(10) Patent No.: US 8,911,603 B2
(45) Date of Patent: Dec. 16, 2014

(54) LED-BASED SCREENER FOR PHOTOELECTROCHEMICAL MATERIALS DISCOVERY

(75) Inventors: Jay R. Winkler, Pasadena, CA (US); Gates R. Winkler, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 37 days.

(21) Appl. No.: 13/550,988

(22) Filed: Jul. 17, 2012

(65) Prior Publication Data

US 2013/0020197 A1 Jan. 24, 2013

Related U.S. Application Data

(60) Provisional application No. 61/510,683, filed on Jul. 22, 2011.

(51) Int. Cl.
*G01N 27/403* (2006.01)
*G01N 27/30* (2006.01)

(52) U.S. Cl.
CPC .................................. *G01N 27/305* (2013.01)
USPC ..... 204/406; 422/82.01; 422/68.1; 435/287.1

(58) Field of Classification Search
CPC ........................... G01N 27/403; G01N 27/305
USPC .............. 204/406; 356/344; 422/68.1, 82.01; 435/287.1
See application file for complete search history.

(56) References Cited

U.S. PATENT DOCUMENTS

2004/0152067 A1* 8/2004 Wang et al. .................. 435/4
2005/0142033 A1* 6/2005 Glezer et al. ................ 422/58

OTHER PUBLICATIONS

Dasgupta et al. (Analytica Chimica 500, 2003, 337-364).*
Winkler et la., Rev. Sci. Instrum. 82, 2011, 114101.*

* cited by examiner

*Primary Examiner* — Jennifer Dieterle
(74) *Attorney, Agent, or Firm* — Milstein Zhang & Wu LLC; Joseph B. Milstein (57) ABSTRACT

An LED-based materials analysis apparatus that measures the photoelectrochemical response of materials to illumination. The apparatus uses an array of light sources such as a plurality of LEDs that provide light of desired wavelengths to illuminate one or more samples of materials of interest that are immersed in an electrolyte. A measurement circuit is connected between a transparent conductor attached to each sample of interest and a counter electrode. In some measurements, a third, standard electrode may be connected to the measurement circuit. A pulsing circuit that operates the LEDs causes each sample to be tested according to a predetermined sequence. Data is collected using a programmable computer operating under the control of instructions recorded on a machine readable medium. The data is analyzed and is available to be displayed to a user, recorded in a database, or communicated to another apparatus or process.

9 Claims, 11 Drawing Sheets

FIG. 1

PRIOR ART

LED-BASED SCREENER FOR PHOTOELECTROCHEMICAL MATERIALS DISCOVERY

CROSS-REFERENCE TO RELATED APPLICATIONS

This application claims priority to and the benefit of co-pending U.S. provisional patent application Ser. No. 61/510,683 filed Jul. 22, 2011 which application is incorporated herein by reference in its entirety.

STATEMENT REGARDING FEDERALLY FUNDED RESEARCH OR DEVELOPMENT

This invention was made with government support under CHE0947829 awarded by the National Science Foundation. The government has certain rights in the invention.

FIELD OF THE INVENTION

The invention relates to materials analysis in general and particularly to systems and methods for analyzing photoactive materials.

BACKGROUND OF THE INVENTION

The increasing costs and negative environmental impact of fossil-fuel based energy production are driving the search for sustainable alternative energy sources. Solar radiation is one source that has the potential to meet the projected energy demand in the $21^{st}$ century. See H. B. Gray, Nature Chemistry 1, 7 (2009); N. S. Lewis and D. G. Nocera, Proc. Natl. Acad. Sci. USA 103, 15729 (2006). Photovoltaic (PV) solar energy conversion devices dominate the market, with 13.9 GW of generating capacity installed worldwide through 2008 (1.1 GW in the United States). See S. Price and R. Margolis, 2008 *Solar Technologies Market Report*, Department of Energy (2010), pp. 119.

The mismatch between power production capability and demand is a critical limitation of PV devices: the loss of power generation at night is the most obvious example. One alternative involves the conversion of radiative solar energy into a chemical fuel that can be produced when sunlight is available and consumed when it is needed. Solar water splitting to produce hydrogen and oxygen has long been a primary research objective in this area. The chemistry of water splitting requires catalysts that can couple the individual electrons and holes generated by light absorption to the multielectron redox reactions involved in the production of hydrogen and oxygen. In the ideal case, a single material will perform both light absorption and multielectron redox catalysis. Combinatorial methods are well-suited to the challenge of discovering new materials with the potential to effect photoelectrochemical (PE) water splitting. See M. Woodhouse and B. A. Parkinson, Chemistry of Materials 20, 2495 (2008); M. Woodhouse and B. A. Parkinson, Chem. Soc. Rev. 38, 197 (2009).

There is a need for systems and methods for efficient and rapid screening of candidate photoactive materials as electrode materials for solar fuels production.

SUMMARY OF THE INVENTION

According to one aspect, the invention features an LED-based apparatus for measuring photoelectrically active materials. The apparatus comprises a plurality of LEDs, the plurality of LEDs arranged in a spatially defined array, each of the plurality of LEDs configured to provide illumination having a desired range of wavelengths, each of the plurality of LEDs configured to illuminate a location in registry with the LED, each of the plurality of LEDs having two terminals, each of the plurality of LEDs configured to be individually addressed for the purpose of illuminating the plurality of locations in a predetermined sequence; a pulsing circuit configured to generate an electrical pulse sufficient to operate a respective one of the plurality of LEDs, the pulsing circuit having a terminal configured to control an illumination current of the respective one of the plurality of LEDs at a controlled voltage and a terminal configured to be connected to a reference voltage, the pulsing circuit configured to be connected to the two terminals of each of the plurality of LEDs in the predetermined sequence; an electrochemical cell configured to receive at least one specimen of interest, the specimen of interest comprising a material to be examined for electrochemical activity; the electrochemical cell comprising a transparent specimen holder configured to receive the at least one specimen of interest, the at least one specimen of interest positioned at a respective one of the locations in registry with a selected one of the plurality of LEDs, the transparent specimen holder having an electrically conductive surface configured to make electrical contact with the at least one specimen of interest, and having a specimen holder electrical contact terminal in electrical communication with the electrically conductive surface; an electrolyte volume configured to contain an electrolyte; and a counter electrode having a counter electrode electrical terminal, the transparent specimen holder, the electrolyte volume and the counter electrode configured to provide a cell in which a photoelectrochemical measurement of the at least one specimen of interest can be conducted; a potentiostat configured to measure a photoelectrochemical signal generated in response to an illumination of a respective one of the locations in registry with the LED, the potentiostat connected to the specimen holder electrical contact terminal and to the counter electrode electrical terminal; and a general purpose programmable computer having a set of instructions recorded on a machine-readable medium, the general purpose programmable computer configured to receive the photoelectrochemical signal, configured to analyze the photoelectrochemical signal to obtain a result, and configured to perform at least one of recording the photoelectrochemical signal, displaying the result to a user, and recording the result.

In one embodiment, at least one of the plurality of LEDs is configured to provide white light illumination.

In another embodiment, at least one of the plurality of LEDs is configured to provide colored light illumination.

In yet another embodiment, at least one of the plurality of LEDs configured to provide colored light illumination includes an LED and a filter having a pass band.

In still another embodiment, the transparent specimen holder comprises a non-conductive transparent plate and a conductive transparent layer thereon.

In a further embodiment, the apparatus further comprises a reference electrode configured to be in contact with the electrolyte and configured to be electrically connected to the potentiostat.

In yet a further embodiment, the plurality of LEDs is disposed in an array having rows and columns.

In an additional embodiment, the plurality of LEDs is disposed in an 8×8 array.

In one more embodiment, the said plurality of LEDs comprises $2^N$ LEDs, where N is an integer greater than 0.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

Combinatorial approaches for targeted discovery of new materials require rapid screening systems to evaluate large numbers of new material compositions. High-throughput combinatorial materials discovery is a capital-intensive undertaking requiring sophisticated robotic sample preparation and rapid screening assays. A distributed approach to combinatorial materials discovery can achieve similar goals by increasing the breadth of participation and reducing the size of the capital investment. The discovery of new photoactive materials for solar fuels production demands a screening device to probe materials for electrochemical current production upon irradiation with visible light. We have developed a system that uses an array of pulsed light-emitting diodes synchronized with a two-electrode potentiostat that can measure the photoelectrochemical responses of combinatorial sample arrays deposited on glass plates coated with a transparent conducting layer. Compared to raster scanning methods, this LED system trades spatial resolution for a substantial reduction in scan time.

The rich diversity of the chemical elements ensures that a virtually limitless array of new materials with interesting and important chemical and physical properties remains to be discovered. Metal-oxide materials are likely candidates for water-splitting photoanodes. Every element of the periodic table, except fluorine and the noble gases, will combine with oxygen. The broadest possible search for water splitting photoanodes could include as many as 71 elements: alkali and alkaline earth metals (12 elements); transitions metals from rows 1-3, except Technetium, Tc (29); post-transition elements from groups 13-16 and rows 3-6 (16); and the lanthanides (14). Searching through simple binary metal oxides would likely not require special methods, but once mixed-metal oxide materials are considered, the size of the combinatorial space becomes sizeable. As noted by Parkinson and coworkers,[4,5] high-temperature superconducting materials conveniently illustrate the problem. The first high-$T_c$ material, found in the LaBaCuO system, is an oxide of three different metals. See J. G. Bednorz and K. A. Müller, Z. Phys. B64, 189 (1986). Oxide materials composed of four different metals ($HgBa_2Ca_{m-1}Cu_mO_{2m+2+\delta}$, m=1, 2, 3) exhibit $T_c$ values above 120 K. See L. Gao, Y. Y. Xue, F. Chen, Q. Xiong, R. L. Meng, D. Ramirez, C. W. Chu, J. H. Eggert, and H. K. Mao, Phys. Rev. B 50, 4260 (1994). It is not unreasonable, then, to suppose that a photoelectrochemical water oxidation catalyst could contain four or more different metals.

Table I lists the number of possible combinations of the 71 candidate metal elements for n-metal oxides, using standard combinatorial mathematics; once three or more metals are involved the number of combinations becomes considerable. It is to be recognized that the numbers of combinations in Table I are only the number of possible combinations of metals that can be present in a compound having 1 to 5 different metals. The Table does not account for multiple compositions (or phases) in which there are the same two or more metals,

TABLE I

Numbers of possible combinations with oxygen of 71 different metallic elements to form metal oxide materials.

| Metals | 1 | 2 | 3 | 4 | 5 |
|---|---|---|---|---|---|
| Combinations | 71 | 2,485 | 57,155 | 971,635 | 13,019,909 | for example $BaFe_2O_4$ (barium monoferrite, which is orthorhombic in crystal structure) and $BaFe_{12}O_{19}$ (barium hexagonal ferrite). Moreover, the relative amounts of the different metals in the materials often can be varied continuously (for example when compositions are amenable to doping or form solid solutions). Couple this diversity in elemental composition with variations in preparative conditions, and/or phase changes with temperature and pressure, and it becomes clear that a staggering number of materials are available for investigation.

Small groups of scientists using targeted synthetic approaches can hope to explore only a tiny fraction of the vast space of mixed metal oxides. Combinatorial methods represent an obvious alternative approach: a target function is identified and thousands or millions of compounds are screened for activity. See S. Jayaraman, S. H. Baeck, T. F. Jaramillo, A. Kleiman-Shwarsctein, and E. W. McFarland, Rev. Sci. Instrum. 76 (2005). High-throughput combinatorial materials discovery is a capital-intensive undertaking requiring sophisticated robotic sample preparation, rapid screening assays, and informatics development to transform immense quantities of raw experimental data into an intelligible form. Distributed approaches can dramatically increase the breadth of participation in a combinatorial screening program if the capital investment in the apparatus can be reduced. See V. S.

Pande, I. Baker, J. Chapman, S. P. Elmer, S. Khaliq, S. M. Larson, Y. M. Rhee, M. R. Shirts, C. D. Snow, E. J. Sorin, and B. Zagrovic, Biopolymers 68, 91 (2003). A distributed discovery model using LEGO Mindstorm robotics and raster scanning of samples applied to glass plates coated with a conducting layer has been described previously. We have developed an alternative scanning method using arrays of pulsed light emitting diodes (LEDs).

Instrument Design

Figure 1:
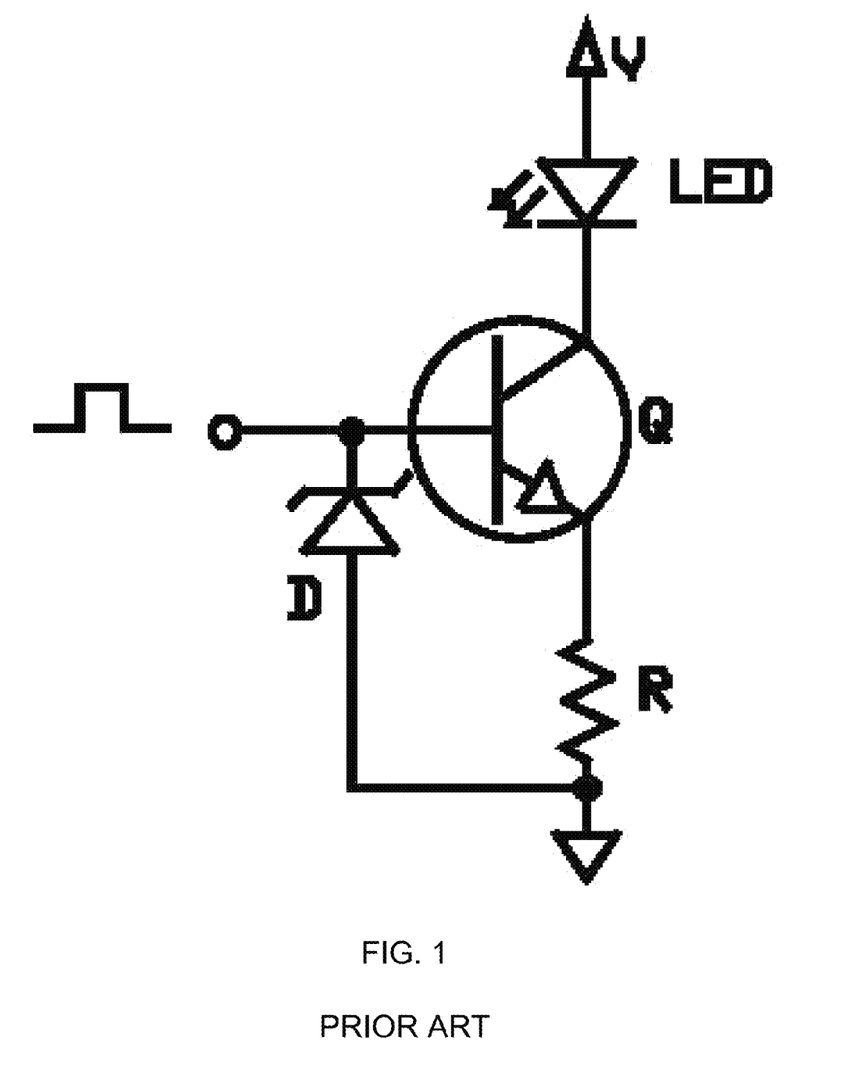
FIG. 1 is a schematic diagram of a npn transistor (Q) sink current source circuit for driving LEDs. The base voltage is limited by a zener diode (D) and the diode current is limited by the emitter resistor (R).

The photoelectrochemical (PE) screener includes two basic components: an array of pulsed LEDs to illuminate samples, and a two-electrode potentiostat for recording photocurrents. The LEDs used in one embodiment of the array (OVLEW1CB9, Optek Technology, Inc.) produce a white light spectrum of high intensity (24,000 mcd at 20 mA) in a narrow beam angle (50% power angle=15°). The heart of the LED pulser is an npn transistor (Q=2N2222A) current sink (FIG. 1). See P. Horowitz and W. Hill, *The Art of Electronics*, Second ed. (Cambridge University Press, Cambridge, 1989). The base voltage to the transistor is limited using a 3.6 V zener diode. The base-to-emitter diode drop produces $V_E$~3 V at the emitter, which is dropped across a resistor (R=39Ω) to ground. The nominal current through the resistor ($I_E$~75 mA) is drawn from the collector, which is held at least ~0.2 V higher than $V_E$. The OVLEW1CB9 narrow beam angle LED is rated at 25 mA continuous forward current, 100 mA peak forward current at 1 kHz, 10% duty cycle, with a 4 V forward drop at 80 mA. Owing to bandwidth limitations in the electrochemical cell, we elected to drive the diodes for 100 ms, but at a rate of less than one pulse per minute per diode.

Figure 2:
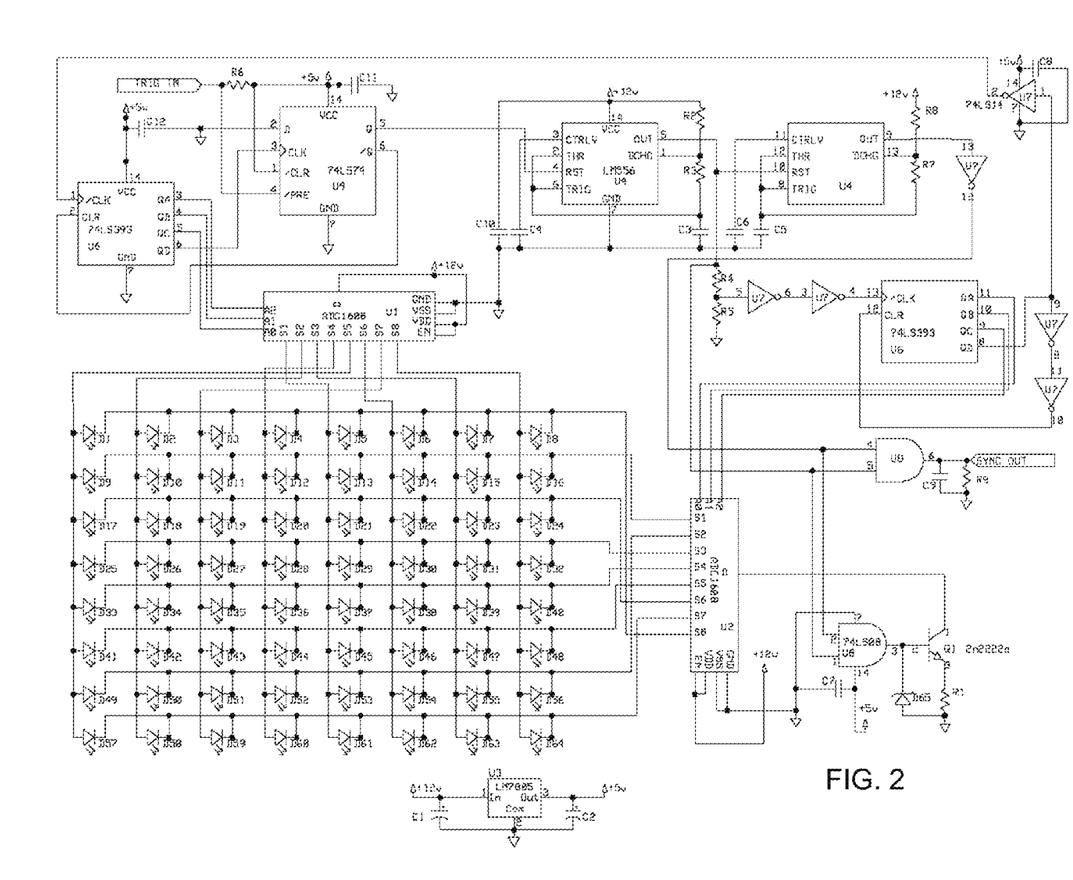
FIG. 2 is a schematic diagram of a pulsed 8×8 LED array circuit.

In the present embodiment, a square 8×8 array of LEDs (0.4 inch center-to-center spacing) was addressed using two 4-bit binary counters (SN74LS393: U6, FIG. 2) controlling two analog multiplexers (ADG1608: U1, U2). In other embodiments, the array can comprise a plurality of LEDs, such as $2^N$ LEDs, where N is an integer greater than 0. In operation, one analog multiplexer selects the row of the array of LEDs that will be pulsed and the other of the analog multiplexers selects the column of the array of LEDS that will be pulsed. The LED having one terminal connected to the selected row and a second terminal connected to the selected column will be illuminated by a pulse. Counter-1 is clocked with the output from an astable oscillator running at ~1Hz (LM556, U4). Counter-2 is clocked with the bit-3 output from counter-1. Bits 0-2 of counters 1 and 2 feed the address lines on multiplexers 1 and 2, respectively. Pulsing is initiated by momentarily pulling the preset line of a flip-flop (SN74LS74, U9) low, driving the output high to enable the oscillator. The flip-flop is clocked by the bit-3 output from counter-2, driving the output low and inhibiting counting. The analog multiplexers select each diode in sequence to connect to the npn transistor collector input. The diodes are illuminated in a predetermined order in which two adjacent locations in the array may not be illuminated in succession to avoid introduction of systematic bias associated with data collection time. The base of the transistor (Q1) is driven high for 100 ms by the output from the second oscillator on the LM556, which is triggered by the output of the first oscillator. In an alternative embodiment, the two analog multiplexers U1 and U2 can be driven by a general purpose programmable computer so as to control the sequence of illumination of the respective LEDs in the LED array in any desired order, by setting the order of the rows and columns that are selected.

If the photocurrent from an illuminated semiconductor exhibits a nonlinear dependence on the excitation flux, then it is possible that pulsed-light sources will produce results that are not representative of behavior expected under steady-state irradiation. Using a thermopile detector and continuous forward current of 26.5 mA, we estimated a 20±5 mW radiant flux from the OVLEW1CB9 LEDs used in this instrument. Extrapolation on the basis of the OVLEW1CB9 data sheet suggests that the flux will be ~60 mW under the pulsed conditions (75 mA) used in the device, corresponding to ~300 mW cm$^{-2}$ for the 5-mm diameter LED. This value compares with the peak insolation of ~100 mW cm$^{-2}$. Although the white-light emitting diode spectral distribution differs markedly from the solar spectrum, the visible light flux produced by the pulsed LEDs in the materials screening device is not dramatically greater than that of the sun at the surface of the earth. Moreover, since negative results typically far outweigh the positive in combinatorial screening, nonlinear photocurrent responses due to the modest LED excitation fluxes are not likely to be a problematic source of false positives. Optionally, one could measure the illumination provided by each LED to prepare a set of reference illumination data for each LED in the array in order to correct for differences in illumination intensity provided by the respective LEDs under pulsed operation.

The pulsed LED array requires one trigger signal to initiate pulsing (TRIG IN), and provides a synchronous output pulse (SYNC OUT) for triggering A/D readouts from the potentiostat. Four additional digital outputs are used to form a 4-bit value representing the hardware version of the device.

Figure 3:
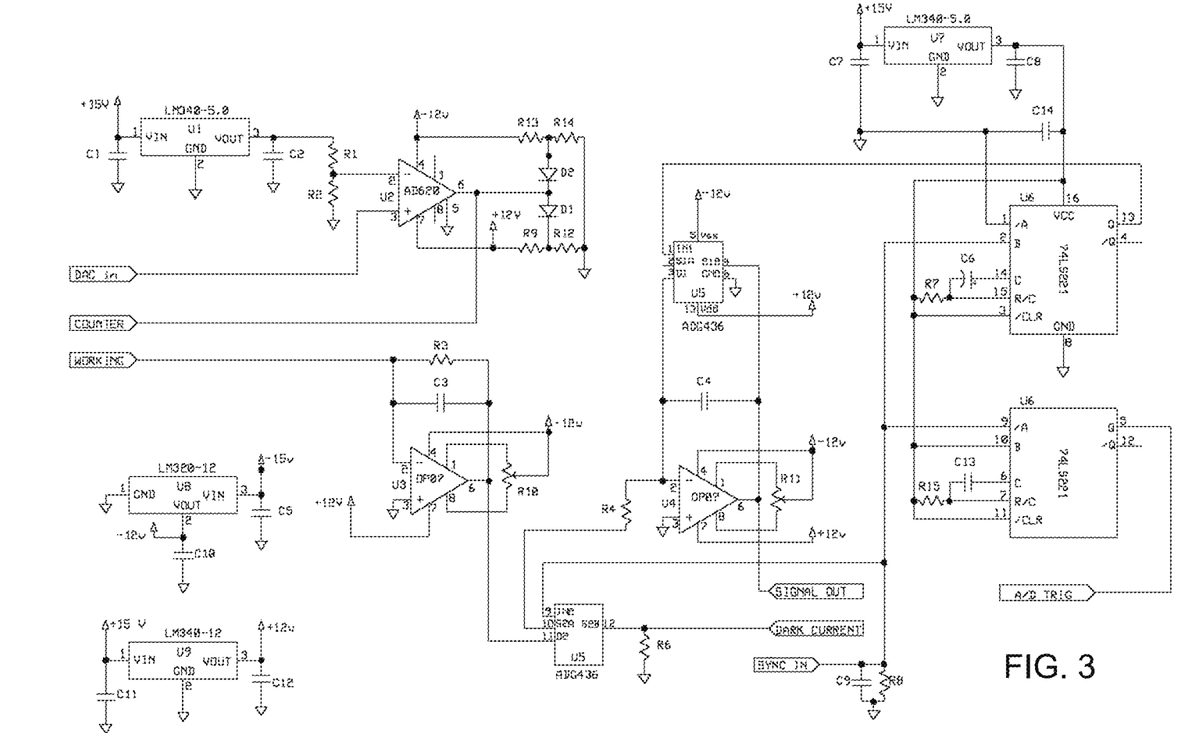
FIG. 3 is a schematic diagram of two-electrode potentiostat circuit.

Samples to be examined are placed in an electrochemical cell as is now described. Using the pulse circuit, the LED array illuminates solid samples adhered to a conducting transparent plate (for example, a glass plate coated with a conductive oxide such as fluorine-doped tin oxide, FTO), immersed in an electrolyte solution held in a container. For operation in which individual samples are illuminated at separate times, there is no need to pattern the conductive oxide. The samples are adhered to the conducting transparent plate in locations that correspond to the locations of the LEDs in the LED array. In any particular analysis, there can be fewer samples present on the plate than there are LEDs. The full electrochemical cell comprises one or more working electrode materials (at least one combinatorial sample on the FTO plate), a voltage source, and a counter electrode. Photocurrents generated in the samples present in the cell are measured using a simple two-electrode potentiostat (FIG. 3). See A. J. Bard and L. R. Faulkner, *Electrochemical Methods: Fundamentals and Applications*, 2nd ed. (John Wiley & Sons, New York, 2001). There is no fundamental reason why a three-electrode potentiostat, wherein applied voltages are defined relative to a reference electrode (for example, SCE, or Ag/AgCl), could not be used as well. Indeed, from an electrochemical perspective it is preferable (but not necessary) to define the potential of the working electrode relative to an accepted standard. One imperative of distributed combinatorial approaches, however, is to minimize cost and complexity for the users. It is in this sense that the two-electrode potentiostat may be better suited to the task than a three-electrode design. The working electrode of the potentiostat is held at virtual ground at the inverting input of a low-offset-voltage operational amplifier (OP07, U3) configured as a 1 V/μA current-to-voltage (I/V) converter. The output from the I/V converter is directed to one analog input (DARK CURRENT) of a National Instruments USB-6008 multifunction I/O card, or to a second OP07 (U4) configured as an integrator. The integrator output (SIGNAL OUT) is directed to a second A/D input on the UBS-6008. The signal path is determined by an analog switch (ADG436) that is controlled by pulses from a monostable (74LS221, U6) clocked by the SYNC OUT signal from the LED array. A second monostable output (A/D TRIG) is used as a hardware trigger for the USB-6008 A/D conversions. Voltage is applied to the counter electrode by an AD620 instrumentation amplifier (U2) driven by the D/A output from the USB-6008 (DAC IN). Diodes (D1, D2) clamp the cell voltage at ~±1.6 V.

In a preferred embodiment, the LED array and potentiostat are contained in separate housings and driven by separate power supplies in order to minimize LED current noise pick-up by the potentiostat. In the present embodiment, a standalone control program (a set of instructions for operating a general purpose programmable computer that are recorded on a machine-readable medium) was written using the MATLAB® programming workbench (available from The MathWorks, Inc., Natick, Mass.) employing the Data Acquisition Toolbox™ and the MATLAB® Compiler Deployment Tool. The program controls the applied potential, reads out background currents, scans the array with signal-averaging, and plots and stores the data in graphical and numerical formats. The program is presented in Appendix I. As will be understood, similar sets of instructions that work in an equivalent manner can be written in other programming languages.

Results

Figure 4A:
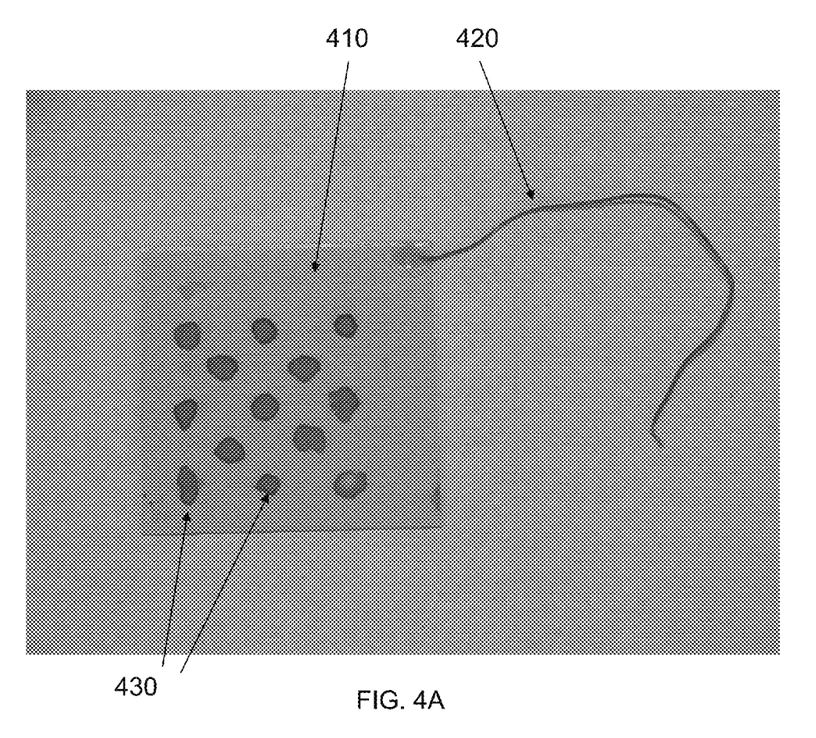
FIG. 4A is an image of a FTO plate spotted with iron oxide test samples for use in a photoelectrochemical materials discovery system.
Figure 4B:
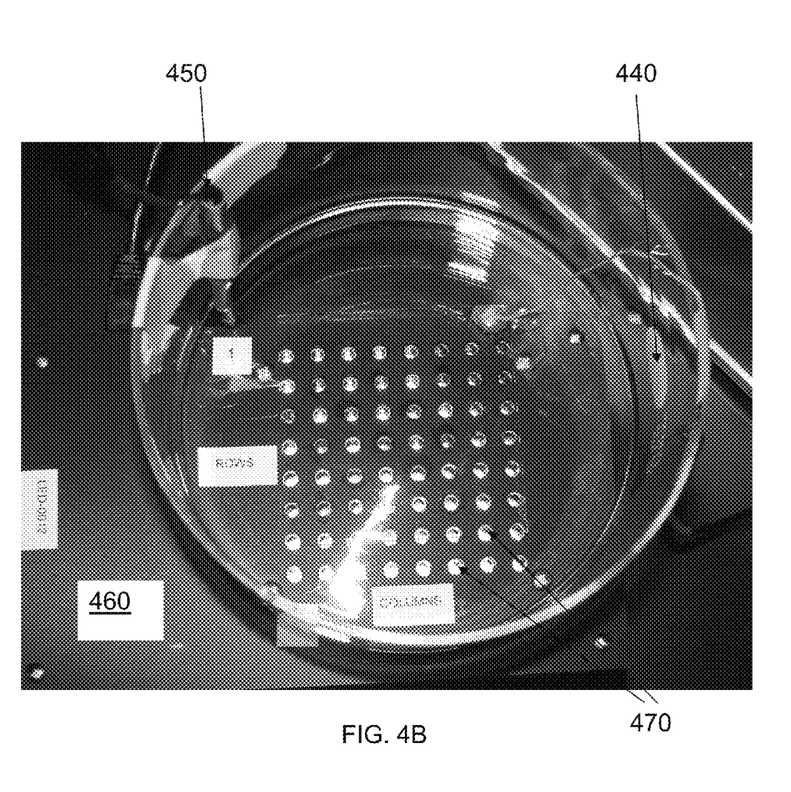
FIG. 4B is an image of a test plate of FIG. 4A in a dish containing electrolyte, positioned above the LED array of the photoelectrochemical materials discovery system.

In the embodiment described, samples for PE screening comprise metal oxides on FTO plates, spotted in spatial alignment with the LED array (see FIG. 4A and FIG. 4B). In FIG. 4A, there is shown a test specimen including a transparent plate 410 with a transparent conductive coating having a conductor 420 in electrical contact with the transparent conductive coating has a plurality of metal oxide samples 430 applied in predetermined locations, each location arranged to be in registry with an LED in an LED array.

FIG. 4B shows the test specimen of FIG. 4A positioned in a transparent container 440 (here a glass beaker) with a graphite counter electrode 450 placed along the sidewall of the container, and located above an LED array built into a housing 460 that contains the LEDs 470 and a pulsing circuit. As can be seen in FIG. 4B, the metal oxide samples 430 are in registry with LEDs 470. In the example illustrated, there are more LEDs 470 than there are metal oxide samples 430. In some embodiments, it is possible to provide a reference electrode (not shown) such as a standard calomel electrode and a three terminal potentiostat (not shown).

The metal oxide samples were prepared by evaporation of aqueous metal salt solutions on FTO, followed by calcining and sintering at 500° C. for ~2 hrs. This aerobic heat treatment accomplishes multiple necessary functions, including oxide formation and adhesion of metal oxide particles to one another and to the conducting glass. The latter step is essential for developing the ohmic contact between the glass electrode and the sample. Different materials may require varying durations and temperatures for optimum electrical contact; this represents another variable in the combinatorial search for new materials. In other embodiments, metals could be deposited using other deposition techniques. Alternatively, samples could be prepared and coated on one side with a layer of FTO or other transparent oxide that is also used on the transparent conducting plate, so that layers of the transparent oxide are adhered to each other to attach the sample of interest. For combinatorial sample screening, each spot corresponds to a different metal salt mixture. A wire is glued to the conducting side of the plate using a silver epoxy. The silver epoxy is then covered with a nonconducting epoxy to prevent electrolysis. Sample plates are held in a large flat-bottomed dish containing electrolyte (for example, 0.1 M NaOH) that allows for easy positioning of the spotted array above the LED array. In the embodiments described, a graphite counter electrode completes the electrical circuit.

Figure 4C:
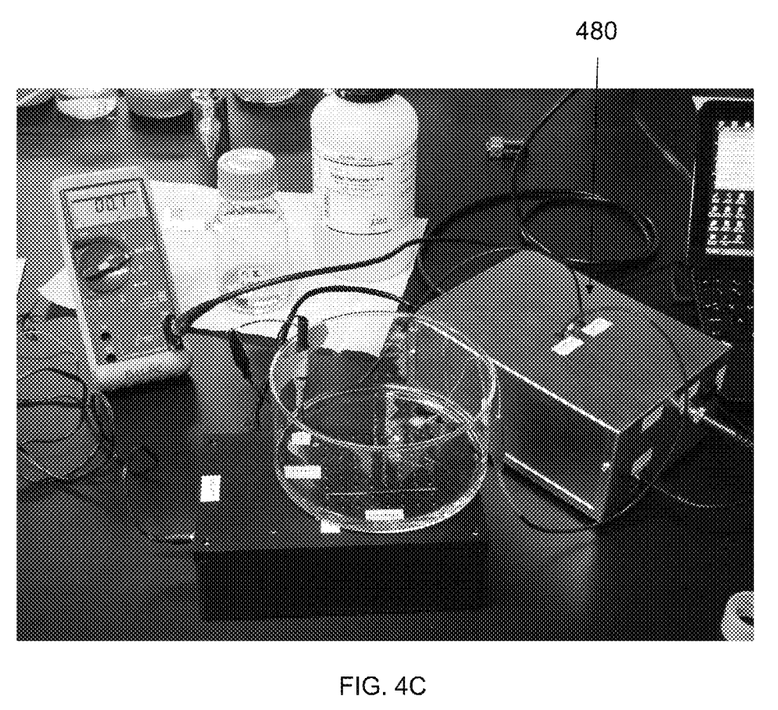
FIG. 4C is an image of a photoelectrochemical materials discovery system that operates according to principles of the invention, including an LED array (black box) and two electrode potentiostat (aluminum box).
Figure 5:
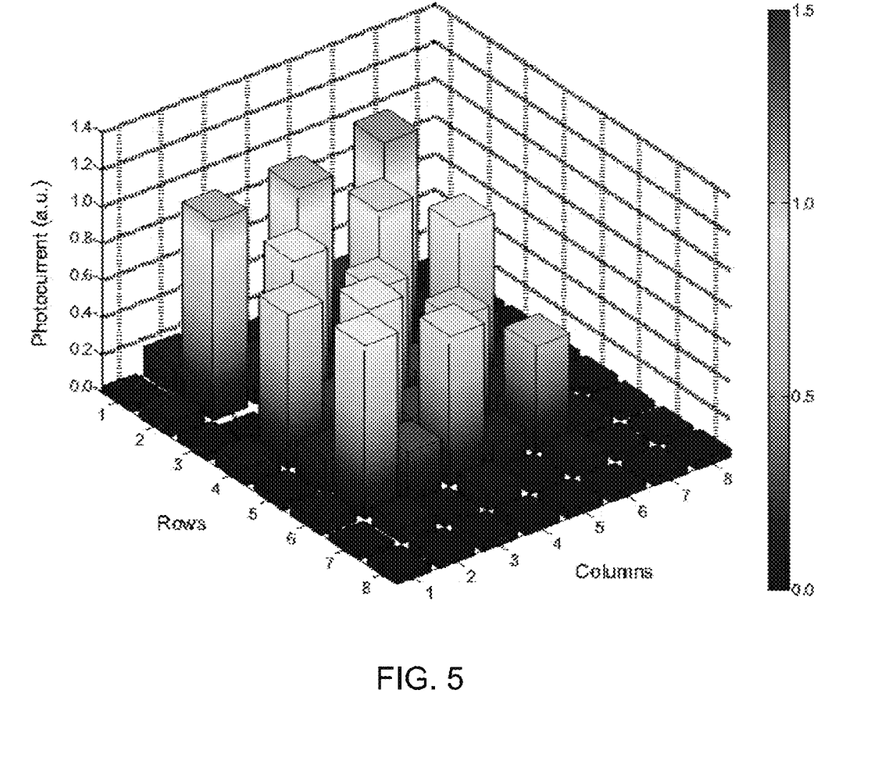
FIG. 5 is a graph of signal-averaged data from ten scans of the iron oxide test plate shown in FIG. 4A. The applied potential was 0.1 V. The smaller blue bars between the tall bars represent interchannel crosstalk.

Hematite is known to provide a reasonable PE response under anodic bias and visible light illumination. Iron oxide prepared by calcination (500° C., 2 hr) of an evaporated ferric nitrate (0.04 M) sample serves as a convenient test plate for the instrument (see FIG. 4C). In FIG. 4C there is shown a two electrode potentiostat 480. The results from the average of ten scans (0.1 V applied potential) are represented by 3D bar graphs in FIG. 5. The heights of the solid bars reflect the integrated photocurrents produced during the 100-ms sample illumination period. Modest crosstalk between diodes results from several factors such as the finite beam angle of the LED; irregular spot size; and imperfect spot alignment on the plate. For initial screening of combinatorial samples, however, the limited amount of crosstalk between LEDs is acceptable. The data acquisition time (~70 sec/scan) is short enough that sample preparation, rather than PE response screening, is rate limiting in the materials discovery process.

The LED array was constructed with white-light emitting diodes to provide the most general screening tool. It is conceivable that a screening project will involve a search for materials that respond to specific colors of light. In this instance an array can be constructed from monochromatic LEDs. We have constructed arrays using blue, green, and amber LEDs for use in refined screening protocols. Larger arrays could be constructed easily by increasing the numbers of hardware counting bits and multiplexer outputs.

This combinatorial materials discovery project was originally conceived to identify new water-splitting materials for solar energy conversion. Many other important chemical transformations lend themselves to PE catalysis. Examples include carbon dioxide reduction and waste water detoxification. See T. Arai, S. Sato, K. Uemura, T. Morikawa, T. Kajino, and T. Motohiro, Chem. Comm. 46, 6944 (2010); H. Selcuk, W. Zaltner, J. J. Sene, M. Bekbolet, and M. A. Anderson, J. Appl. Electrochem. 34, 653 (2004).

Given the results that have been obtained, it is apparent that the LED scanning system described here is well-suited to combinatorial searches for materials that can catalyze these and other refractory chemical reactions.

Figure 6:
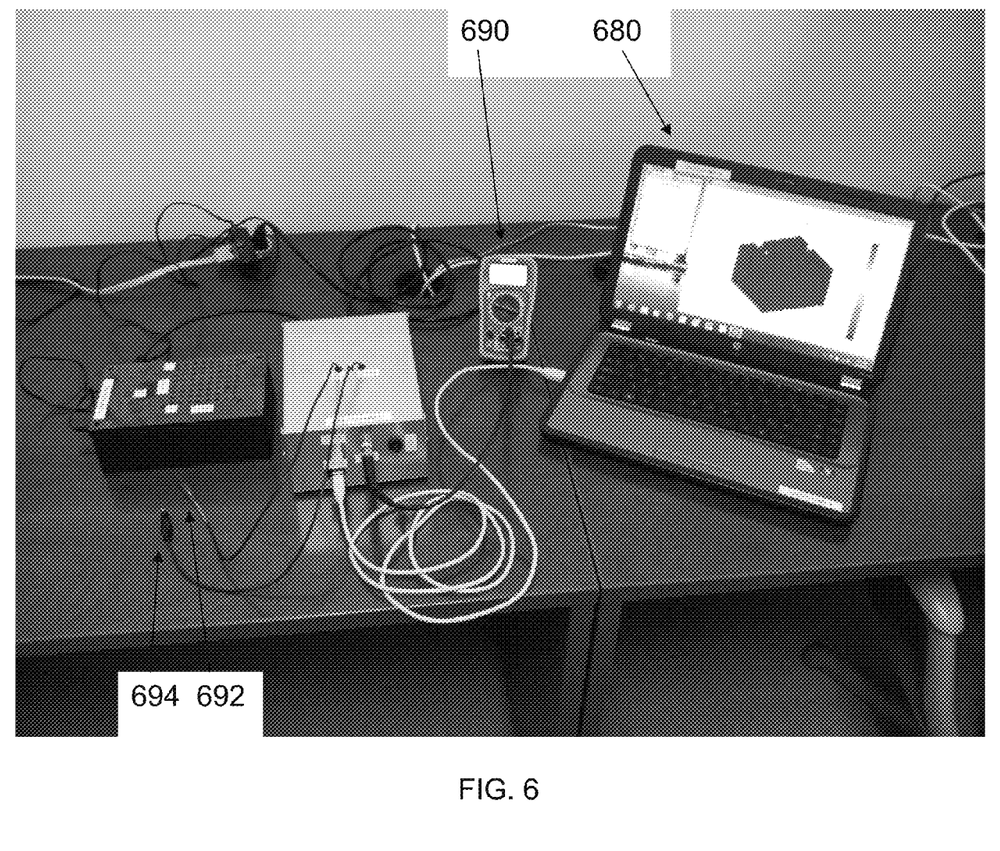
FIG. 6 is an image that shows all of the components of the apparatus.

FIG. 6 is an image that shows all of the components of the apparatus. In FIG. 6, a general purpose programmable computer 680 (here a laptop PC) and a multimeter 690 that can be used to measure the voltage applied by the two electrode potentiostat 480 are shown. The two electrode potentiostat 480 is connected to the sample and the counter electrode with leads 692 and 694.

Figure 7:
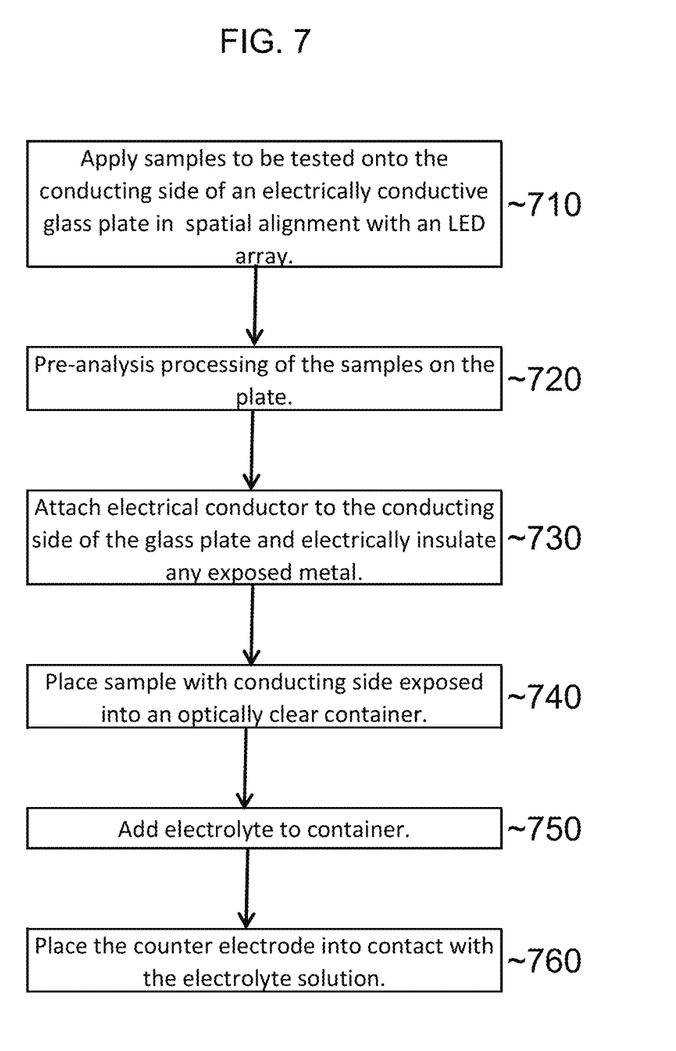
FIG. 7 is a flow diagram illustrating the steps of sample preparation.

FIG. 7 is a flow diagram illustrating the steps of sample preparation. As illustrated in FIG. 7, a sample is prepared by applying samples to be tested onto the conducting side of an electrically conductive glass plate, as shown in Step 710. In the present embodiment this involve placing samples in one or more locations of an 8×8 array in spatial alignment with the 8×8 LED array. As shown in Step 720, one then performs pre-analysis processing of the samples on the plate. Examples of pre-analysis processing include heat treatment and chemical treatment. Step 720 may be an optional step (that is, some samples might not require a pre-analysis processing step). As shown in Step 730, one attaches a wire (or other electrical conductor) to the conducting side of (or conductive layer on) the glass plate. One should preferably cover any exposed metal at this junction with an electrically insulating material (for example, a non-conductive epoxy). The distal end of the wire provides one of the electrical contacts needed to measure the photoelectrochemical characteristics of the individual specimens in the sample. As shown in Step 740, the sample is placed with the conducting side exposed into an optically clear container. In some embodiments, this involves placing the sample with its conducting side up into a flat-bottom, optically clear, container, as shown in FIG. 4B. In some embodiments the sample can be placed in a glass dish. As shown in Step 750, electrolyte is added to the container. In particular, enough electrolyte to cover the upper surface of the plate and to contact the counter electrode should be added. As shown in Step 760, the counter electrode is placed into the container in a location where it will come into contact with the electrolyte solution. The counter electrode includes a contact conductor having a distal end that is a second electrical contact needed to measure the photoelectrochemical characteristics of the individual specimens in the sample.

In different embodiments, some of the steps can be performed in different order. For example Step 730 (connecting an electrical wire to the conductive layer) can be performed before Step 710 (placing specimens on the conductive layer) as long as the location of connection of the wire does not interfere with the location of the samples. As another example, Step 760 (placing the counter electrode into the container in a location where it will come into contact with the electrolyte) could be performed before Step 750, or, if the counter electrode is located in a side well of the container, it could be present even before Step 710 is performed. In some embodiments a reference electrode is also provided. The reference electrode has a conductor attached to it that provides a third electrical contact needed to measure the photoelectrochemical characteristics of the individual specimens in the sample when a three terminal potentiostat is used.

Figure 8:
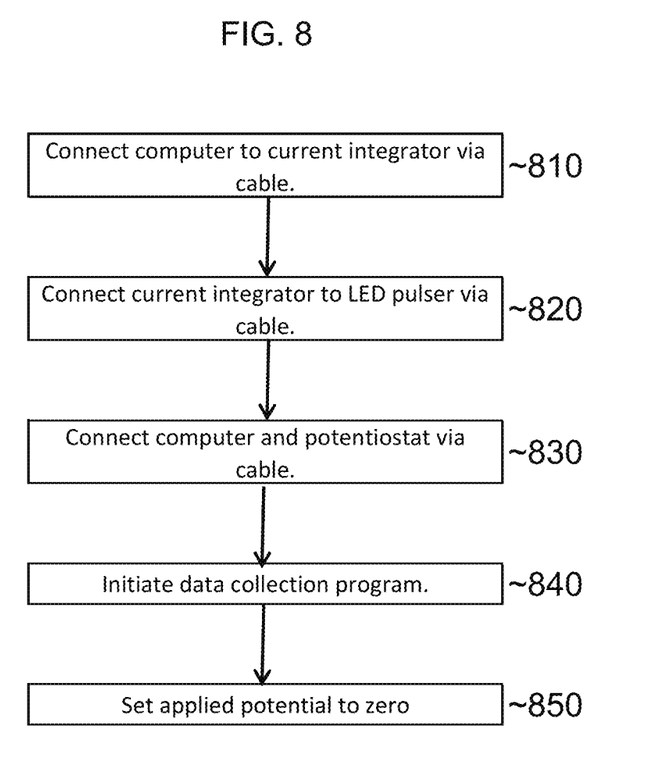
FIG. 8 is a flow diagram illustrating the steps of instrument preparation.

FIG. 8 is a flow diagram illustrating the steps of instrument preparation, or setting up the measurement instrument. As shown in FIG. 8, Step 810 involves connecting the computer to a current integrator via a cable. Step 820 involves connecting a current integrator to the LED pulser via a cable. Step 830 involves connecting the general purpose programmable computer 680 and the potentiostat 480 via cable. Step 840 involves initiating the data collection program that operates on the general purpose programmable computer 680. Step 850 involves setting the applied potential to zero. Again, the steps in FIG. 8 can be performed in different order. For example, the connecting steps 810, 820 and 830 can be performed in any order. If the data collection program is tolerant of disconnected connections (that is, if it recognizes that a connection has not yet been made, and that condition does not cause the data collection program to misbehave), the step of initiating the data collection program can be performed at any point before or after any of steps 810, 820 and 830.

Figure 9:
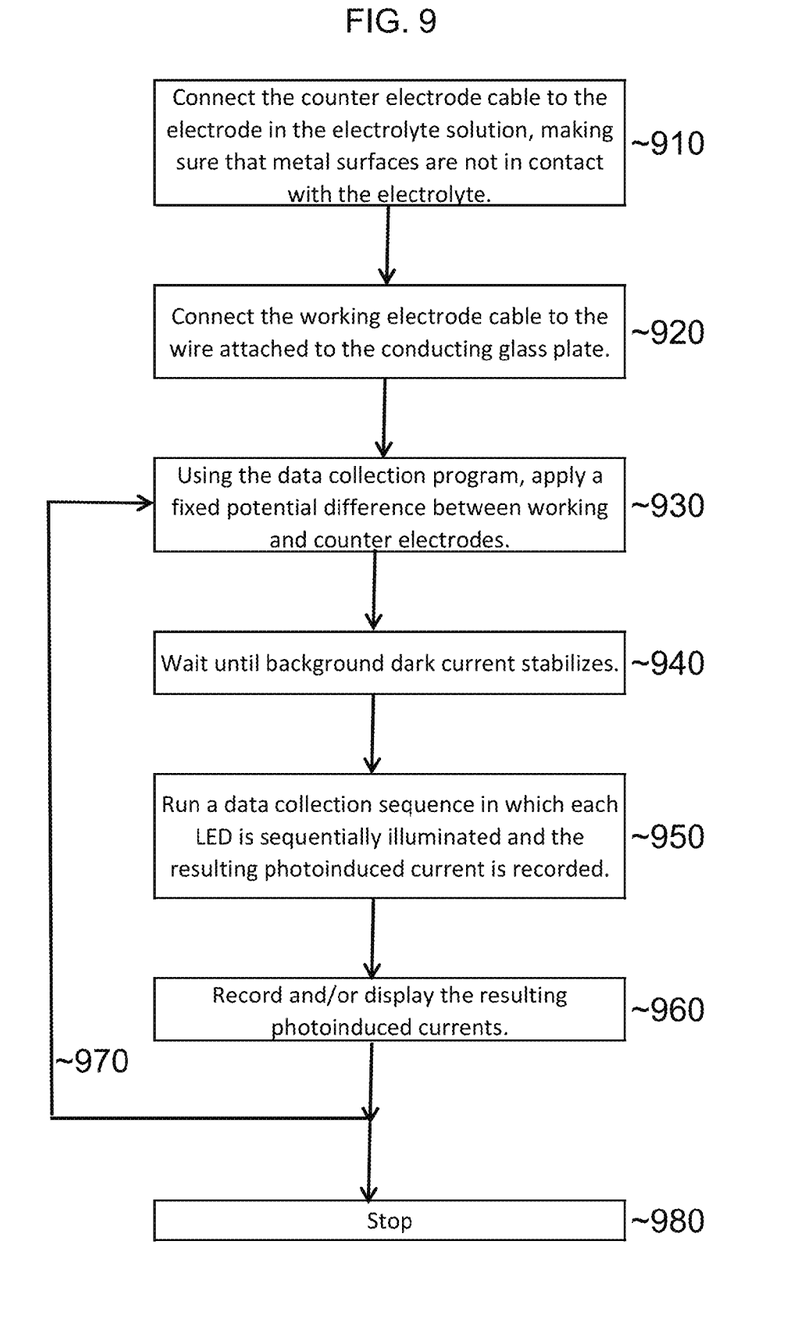
FIG. 9 is a flow diagram illustrating the steps of making a measurement.

FIG. 9 is a flow diagram illustrating the steps of making a measurement. With a sample prepared according to the procedure given in FIG. 7 and a measurement instrument set up according to the procedure in FIG. 8, one proceeds as shown in FIG. 9. Step 910 involves connecting the counter electrode cable to the electrode in the electrolyte solution, making sure that metal surfaces are not in contact with the electrolyte. Step 920 involves connecting the working electrode cable to the wire attached to the conducting glass plate. Step 930 involves using the data collection program to apply a fixed potential difference between working and counter electrodes. Step 940 involves waiting until the background dark current stabilizes. Step 950 involves running a data collection sequence in which each LED is sequentially illuminated and the resulting photoinduced current is recorded. Step 960 involves recording and/or displaying the resulting photoinduced currents, or the photoelectrochemical signals measured by the potentiostat. For example, the results can be plotted in graphical form and displayed to a user. Step 970 involves repeating the measurement for another fixed voltage, illustrated by arrow 970 that implies returning to Step 930 and repeating steps 930, 940, 950 and 960. These steps can be repeated as many times as one cares to do so, or as many times as the general purpose programmable computer is programmed to carry out. After the measurement process has been performed as many times as one desires or as many times as is required to obtain the data that is desired, the measurement process stops at Step 980.

Working Electrode Attributes

A sample to be tested for photoelectrochemical activity needs to be adhered to and in electrical contact with the working electrode. The electrode preferably is optically transparent at least in a range of wavelengths of interest in order to allow light from the pulsed LEDs to reach the sample being tested, and needs to have suitable electrical conductivity. Indium tin oxide (ITO) and fluorine-doped tin oxide (FTO) are examples of suitable choices of materials for the working electrodes.

Counter Electrode Attributes

The counter electrode completes the electrical circuit in the cell. The counter electrode material should be electrically conductive but resistant to corrosion in the electrolyte. Graphite is a suitable choice, but other corrosion-resistant materials such as gold (Au) or platinum (Pt) are expected to function as well.

Electrolyte Attributes

The electrolyte solution must have sufficiently high ionic strength to facilitate current flow in the electrochemical cell. Aqueous solutions with acidic (for example, hydrochloric, perchloric, sulfuric, or nitric acids) or basic (for example, sodium hydroxide, potassium hydroxide) media are suitable. Neutral salt solutions (for example, sodium chloride, sodium phosphate, and sodium sulfate) are suitable as well in some instances. The choice for the pH of the medium depends on the type of photoelectrochemical reaction being screened.

Led Array Attributes

A spatial array of light-emitting-diodes (LEDs) is used to illuminate the various sample compositions being screened. In different embodiments, the shape of the array need not be square, and the number of LEDs need not be 64. There can be more LEDs than samples to be illuminated. Each of the samples to be examined needs to be in geometric registry with at least one LED. White LEDs are a good choice for screening for photoelectrochemical response to the entire visible spectrum, but monochromatic LEDs can be used if photoelectrochemical response to a particular color of light is being probed. Readily available alternative colors are red, amber, green, blue, and violet. Another possible source of illumination in a desired wavelength range is a white LED in conjunction with one or more optical filters, so that a pass band in the range of wavelengths of interest is provided.

Potentiostat Attributes

The illustrative device that has been described is configured as a two electrode potentiostat with the voltage between working and counter electrodes held at a fixed value. Current through this two-electrode circuit is measured. In other embodiments, the instrument also could be configured with a three-electrode potentiostat in which the potential difference between the working and a standard reference electrode (for example, saturated calomel electrode) is held at a fixed value but current flows through the circuit between the working and counter electrodes. The potential difference between working and counter electrodes is not fixed; instead it varies to meet the needs of current flow through the cell.

Sample Attributes

The purpose of the device is rapid screening for photoelectrochemical activity of materials of varying composition. The type of material depends in large part on the type of chemistry to be investigated.

EXAMPLE 1

Water Oxidation Chemistry, $2H_2O \rightarrow 4H^+ + 4e^- + O_2$ or $2HO^- \rightarrow 2H^+ + 4e^- + O_2$ Metal oxides are potential target materials for water oxidation chemistry. The electrolyte contains the substrate ($H_2O$ or $HO^-$). The objective is to screen metal oxides that, upon LED excitation with or without application of a positive bias, will remove four electrons from two water molecules and produce molecular oxygen.

EXAMPLE 2

Water Reduction Chemistry, $2H_2O + 2e^- \rightarrow 2HO^- + H_2$ or $2H^+ + 2e^- \rightarrow H_2$ Metal sulfides and metal alloys are potential target materials for water reduction chemistry. The electrolyte contains the substrate ($H_2O$ or $H^+$). The objective is to screen metal sulfides and alloys that, upon LED excitation with or without application of a negative bias, will add two electrons to water and produce molecular hydrogen.

EXAMPLE 3

Generic Oxidation Chemistry, Substrate+ $H_2O \rightarrow 2H^+ + 2e^- + $ Substrate(O)

Metal oxides are potential target materials for generic substrate oxidation chemistry. The electrolyte contains the dissolved substrate. The objective is to screen metal oxides that, upon LED excitation with or without application of a positive bias, will remove two electrons from the substrate and deliver an oxygen atom to the substrate.

A potential substrate is methane with the production of methanol:

$$CH_4 + H_2O \rightarrow CH_3OH + 2H^+ + 2e^-$$

EXAMPLE 4

Generic Reduction Chemistry, Substrate+$2H^+ + 2e^- \rightarrow$ Substrate($H_2$)

Metal sulfides and metal alloys are potential target materials for generic reduction chemistry. The electrolyte contains the dissolved substrate. The objective is to screen metal sulfides and alloys that, upon LED excitation with or without application of a negative bias, will add two electrons and two protons to the substrate. A potential substrate is carbon dioxide with the production of formic acid:

$$CO_2 + 2H^+ + 2e^- \rightarrow HCO_2H$$

The LED scanning array sacrifices the high spatial resolution of raster scanning in favor of data acquisition speed in a combinatorial search for new PE materials. The optimum combinatorial materials discovery protocol is a hierarchical approach whereby coarse screening with the LED array is used first to identify PE-active combinations of elements. Promising samples prepared with finer mixing gradients would then undergo a second level of screening, either with the LED array or a raster scanner, to isolate combinations with maximum activity.

Definitions

Unless otherwise explicitly recited herein, any reference to an electronic signal or an electromagnetic signal (or their equivalents) is to be understood as referring to a non-volatile electronic signal or a non-volatile electromagnetic signal.

Recording the results from an operation or data acquisition, such as for example, recording results at a particular frequency or wavelength, is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (for example, floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (for example, OCR and magnetically encoded symbols) and machine-readable symbols such as one and two dimensional bar codes. Recording image data for later use (for example, writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein, so long as at least some of the implementation is performed in hardware.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. An LED-based apparatus for measuring photoelectrically active materials, comprising:
a plurality of LEDs, said plurality of LEDs arranged in a spatially defined array, each of said plurality of LEDs configured to provide illumination having a desired range of wavelengths, each of said plurality of LEDs configured to illuminate a location in registry with said LED, each of said plurality of LEDs having two terminals, each of said plurality of LEDs configured to be individually addressed for the purpose of illuminating said plurality of locations in a predetermined sequence;
a pulsing circuit configured to generate an electrical pulse sufficient to operate a respective one of said plurality of LEDs, said pulsing circuit having a terminal configured to control an illumination current of said respective one of said plurality of LEDs at a controlled voltage and a terminal configured to be connected to a reference voltage, said pulsing circuit configured to be connected to said two terminals of each of said plurality of LEDs in said predetermined sequence;
an electrochemical cell configured to receive at least one specimen of interest, said specimen of interest comprising a material to be examined for electrochemical activity; said electrochemical cell comprising;
a transparent specimen holder configured to receive said at least one specimen of interest, said at least one specimen of interest positioned at a respective one of said locations in registry with a selected one of said plurality of LEDs, said transparent specimen holder having an electrically conductive surface configured to make electrical contact with said at least one specimen of interest, and having a specimen holder electrical contact terminal in electrical communication with said electrically conductive surface;
an electrolyte volume configured to contain an electrolyte; and
a counter electrode having a counter electrode electrical terminal, said transparent specimen holder, said electrolyte volume and said counter electrode configured to provide a cell in which a photoelectrochemical measurement of said at least one specimen of interest can be conducted;
a potentiostat configured to measure a photoelectrochemical signal generated in response to an illumination of a respective one of said locations in registry with said LED, said potentiostat connected to said specimen holder electrical contact terminal and to said counter electrode electrical terminal; and
a general purpose programmable computer having a set of instructions recorded on a machine-readable medium, said general purpose programmable computer configured to receive said photoelectrochemical signal, configured to analyze said photoelectrochemical signal to obtain a result, and configured to perform at least one of recording said photoelectrochemical signal, displaying said result to a user, and recording said result.

2. The LED-based apparatus for measuring photoelectrically active materials of claim 1, wherein at least one of said plurality of LEDs is configured to provide white light illumination.

3. The LED-based apparatus for measuring photoelectrically active materials of claim 1, wherein at least one of said plurality of LEDs is configured to provide colored light illumination.

4. The LED-based apparatus for measuring photoelectrically active materials of claim 3, wherein at least one of said plurality of LEDs configured to provide colored light illumination includes an LED and a filter having a pass band.

5. The LED-based apparatus for measuring photoelectrically active materials of claim 1, wherein said transparent specimen holder comprises a non-conductive transparent plate and a conductive transparent layer thereon.

6. The LED-based apparatus for measuring photoelectrically active materials of claim 1, further comprising a reference electrode configured to be in contact with said electrolyte and configured to be electrically connected to said potentiostat.

7. The LED-based apparatus for measuring photoelectrically active materials of claim 1, wherein said plurality of LEDs is disposed in an array having rows and columns.

8. The LED-based apparatus for measuring photoelectrically active materials of claim 1, wherein said plurality of LEDs is disposed in an 8×8 array.

9. The LED-based apparatus for measuring photoelectrically active materials of claim 1, wherein said plurality of LEDs comprises $2^N$ LEDs, where N is an integer greater than 0.

* * * * *